United States Patent
Zhong et al.

(10) Patent No.: US 6,709,706 B2
(45) Date of Patent: Mar. 23, 2004

(54) HYDROPHILIC COATING AND SUBSTRATES COATED THEREWITH HAVING ENHANCED DURABLITY AND LUBRICITY

(75) Inventors: Shengping Zhong, Northborough, MA (US); George Nunez, Miami, FL (US); Eric Welch, Miramar, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/387,380

(22) Filed: Mar. 14, 2003

(65) Prior Publication Data

US 2003/0162032 A1 Aug. 28, 2003

Related U.S. Application Data

(62) Division of application No. 09/876,556, filed on Jun. 7, 2001, now Pat. No. 6,558,798, which is a continuation-in-part of application No. 09/457,955, filed on Dec. 9, 1999, now Pat. No. 6,468,649, which is a continuation-in-part of application No. 08/929,948, filed on Sep. 15, 1997, now Pat. No. 6,048,620, which is a division of application No. 08/392,141, filed on Feb. 22, 1995, now Pat. No. 5,702,754.

(51) Int. Cl.⁷ ................................................. B05D 3/04
(52) U.S. Cl. ........................ 427/333; 427/355; 427/337
(58) Field of Search .......................... 427/412.1, 393.5, 427/2.1, 2.3, 333, 355, 337, 340

(56) References Cited

U.S. PATENT DOCUMENTS

| | | |
|---|---|---|
| 3,663,288 A | 5/1972 | Miller |
| 3,779,792 A | 12/1973 | Stoy et al. |
| 4,047,957 A | 9/1977 | De Winter et al. |
| 4,069,352 A | 1/1978 | Parson, Jr. |
| 4,100,309 A | 7/1978 | Micklus et al. |
| 4,119,094 A * | 10/1978 | Micklus et al. .......... 128/132 R |
| 4,177,038 A | 12/1979 | Biebricher et al. |
| 4,263,188 A | 4/1981 | Hampton et al. |
| 4,306,998 A | 12/1981 | Wenzel et al. |
| 4,373,009 A | 2/1983 | Winn |
| 4,378,435 A | 3/1983 | Takagi et al. |
| 4,387,024 A | 6/1983 | Kurihara et al. |
| 4,391,797 A | 7/1983 | Folkman et al. |
| 4,459,317 A | 7/1984 | Lambert |
| 4,487,808 A | 12/1984 | Lambert |
| 4,500,676 A | 2/1985 | Balazs et al. |
| 4,536,179 A | 8/1985 | Anderson et al. |
| 4,539,234 A | 9/1985 | Sakamoto et al. |
| 4,548,844 A | 10/1985 | Podell et al. |
| 4,600,652 A | 7/1986 | Solomon et al. |
| 4,642,267 A | 2/1987 | Creasy et al. |
| 4,666,437 A | 5/1987 | Lambert |
| 4,675,361 A | 6/1987 | Ward, Jr. |
| 4,692,352 A | 9/1987 | Huddleston |
| 4,705,709 A | 11/1987 | Vailancourt |
| 4,721,117 A | 1/1988 | Mar et al. |
| 4,748,986 A | 6/1988 | Morrison et al. |
| 4,768,507 A | 9/1988 | Fischell et al. |
| 4,770,664 A | 9/1988 | Gogolewski |
| 4,833,014 A | 5/1989 | Linder et al. |
| 4,841,976 A | 6/1989 | Packard et al. |
| 4,867,173 A | 9/1989 | Leoni |
| 4,876,126 A | 10/1989 | Takemura et al. |
| 4,884,579 A | 12/1989 | Engelson |
| 4,923,464 A | 5/1990 | DiPisa, Jr. |
| 4,925,698 A | 5/1990 | Klausner et al. |
| 4,943,460 A | 7/1990 | Markle et al. |

(List continued on next page.)

FOREIGN PATENT DOCUMENTS

| | | |
|---|---|---|
| AU | 556 350 | 10/1983 |
| AU | 556 351 | 10/1986 |
| EP | 0 093 094 | 11/1983 |

(List continued on next page.)

OTHER PUBLICATIONS

Bartoli et al., "In Vitro and In Vivo Antitumoral Activity of Free, and Encapsulated Taxol", J. Microencapsulation, vol. 7, No. 2 (1990) pp. 191–197.

(List continued on next page.)

Primary Examiner—Merrick Dixon
(74) Attorney, Agent, or Firm—Kenyon & Kenyon

(57) ABSTRACT

A substrate, such as a catheter or a guide wire, or a portion of the substrate is provided with a lubricous, hydrophilic abrasion-resistant coating by: (a) coating the substrate with a first aqueous coating composition having an aqueous dispersion or emulsion of a polymer having organic acid functional groups and a polyfunctional crosslinking agent having functional groups capable of reacting with organic acid groups, and drying the coating to obtain a substantially water-insoluble coating layer having excess polyfunctional including functional groups being reactive with organic acid groups remaining; and (b) contacting the dried water-insoluble coating layer with a second aqueous coating composition having an aqueous solution or dispersion of a hydrophilic polymer having organic acid functional groups, a polymer having organic acid functional groups and a polyfunctional crosslinking agent having functional groups capable of reacting with organic acid groups, and drying the combined coating to form an intermediate coating, whereby the polymer and the hydrophilic polymer of the second composition become bonded to the polymer of the first coating composition through the excess crosslinking agent; and (c) contacting the dried intermediate coating with a third aqueous coating composition having an aqueous solution or dispersion of a hydrophilic polymer having organic acid functional groups, and drying the combined coatings, the hydrophilic polymer of the third coating composition thereby becoming bonded to the polymers of the second coating composition through the excess crosslinking agent. The dryings can be carried out at ambient (room) temperature.

22 Claims, No Drawings

U.S. PATENT DOCUMENTS

| | | |
|---|---|---|
| 4,959,074 A | 9/1990 | Halpern et al. |
| 4,964,409 A | 10/1990 | Tremulis |
| 4,969,890 A | 11/1990 | Sugita et al. |
| 4,980,231 A | 12/1990 | Baker et al. |
| 4,994,071 A | 2/1991 | MacGregor |
| 5,002,582 A | 3/1991 | Guire et al. |
| 5,007,928 A | 4/1991 | Okamura et al. |
| 5,008,363 A | 4/1991 | Mallon et al. |
| 5,019,096 A | 5/1991 | Fox, Jr. et al. |
| 5,026,607 A | 6/1991 | Kiezulas |
| 5,037,656 A | 8/1991 | Pitt et al. |
| 5,037,677 A | 8/1991 | Halpern et al. |
| 5,040,543 A | 8/1991 | Badera et al. |
| 5,041,100 A | 8/1991 | Rowland et al. |
| 5,049,393 A | 9/1991 | Noon et al. |
| 5,049,403 A | 9/1991 | Larm et al. |
| 5,057,371 A | 10/1991 | Canty et al. |
| 5,061,750 A | 10/1991 | Feijen et al. |
| 5,066,705 A | 11/1991 | Wickert |
| 5,067,489 A | 11/1991 | Lind |
| 5,069,217 A | 12/1991 | Fleischhacker, Jr. |
| 5,069,226 A | 12/1991 | Yamauchi et al. |
| 5,079,093 A | 1/1992 | Akashi et al. |
| 5,080,683 A | 1/1992 | Sulc et al. |
| 5,080,924 A | 1/1992 | Kamel et al. |
| 5,084,315 A | 1/1992 | Karimi et al. |
| 5,091,205 A * | 2/1992 | Fan ............................... 427/2 |
| 5,092,885 A | 3/1992 | Yamada et al. |
| 5,102,401 A | 4/1992 | Lambert et al. |
| 5,102,402 A | 4/1992 | Dror et al. |
| 5,102,417 A | 4/1992 | Palmax |
| 5,105,010 A | 4/1992 | Sundararaman et al. |
| 5,107,852 A | 4/1992 | Davidson et al. |
| 5,128,170 A | 7/1992 | Matsuda et al. |
| 5,129,890 A | 7/1992 | Bates et al. |
| 5,132,108 A | 7/1992 | Narayanan et al. |
| 5,133,742 A | 7/1992 | Pinchuk |
| 5,160,790 A | 11/1992 | Elton |
| 5,163,958 A | 11/1992 | Pinchuk |
| 5,211,183 A | 5/1993 | Wilson |
| 5,213,111 A | 5/1993 | Cook et al. |
| 5,217,026 A | 6/1993 | Stoy et al. |
| 5,222,971 A | 6/1993 | Willard et al. |
| 5,225,248 A | 7/1993 | Stephenson |
| 5,240,994 A | 8/1993 | Brink et al. |
| 5,241,970 A | 9/1993 | Johlin, Jr. et al. |
| 5,243,996 A | 9/1993 | Hall |
| 5,250,613 A | 10/1993 | Bergstrom et al. |
| 5,263,992 A | 11/1993 | Guire |
| 5,266,359 A | 11/1993 | Spielvogel |
| 5,272,012 A | 12/1993 | Opolski |
| 5,275,173 A | 1/1994 | Samson et al. |
| 5,282,823 A | 2/1994 | Schwartz et al. |
| 5,290,585 A | 3/1994 | Elton |
| 5,304,121 A | 4/1994 | Sahatjian |
| 5,304,140 A | 4/1994 | Kugo et al. |
| 5,322,520 A | 6/1994 | Milder |
| 5,324,261 A | 6/1994 | Amundson et al. |
| 5,328,954 A | 7/1994 | Sarangapani |
| 5,342,348 A | 8/1994 | Kaplan |
| 5,342,621 A | 8/1994 | Eury |
| 5,350,800 A | 9/1994 | Verhoeven et al. |
| 5,360,397 A | 11/1994 | Pinchuk |
| 5,366,505 A | 11/1994 | Farber |
| 5,370,614 A | 12/1994 | Amundson et al. |
| 5,380,299 A | 1/1995 | Fearnot et al. |
| 5,383,928 A | 1/1995 | Scott et al. |
| 5,389,533 A | 2/1995 | von Gentzkow et al. |
| 5,403,750 A | 4/1995 | Braatz et al. |
| 5,419,760 A | 5/1995 | Narciso, Jr. |
| 5,423,885 A | 6/1995 | Williams |
| 5,443,458 A | 8/1995 | Eury |
| 5,443,496 A | 8/1995 | Schwartz et al. |
| 5,447,724 A | 9/1995 | Helmus et al. |
| 5,449,372 A | 9/1995 | Schmaltz et al. |
| 5,449,382 A | 9/1995 | Dayton |
| 5,464,450 A | 11/1995 | Buscemi et al. |
| 5,464,650 A | 11/1995 | Berg et al. |
| 5,478,676 A | 12/1995 | Turi et al. |
| 5,496,581 A | 3/1996 | Yianni et al. |
| 5,510,443 A | 4/1996 | Shaffer et al. |
| 5,512,055 A | 4/1996 | Domb et al. |
| 5,514,154 A | 5/1996 | Lau et al. |
| 5,527,337 A | 6/1996 | Stack et al. |
| 5,541,167 A | 7/1996 | Hsu et al. |
| 5,545,208 A | 8/1996 | Wolff et al. |
| 5,562,922 A | 10/1996 | Lambert |
| 5,567,495 A | 10/1996 | Modak et al. |
| 5,569,463 A | 10/1996 | Helmus et al. |
| 5,571,166 A | 11/1996 | Dinh et al. |
| 5,575,818 A | 11/1996 | Pinchuk |
| 5,576,072 A | 11/1996 | Hostettler et al. |
| 5,578,075 A | 11/1996 | Dayton |
| 5,591,224 A | 1/1997 | Schwartz et al. |
| 5,591,227 A | 1/1997 | Dinh et al. |
| 5,599,352 A | 2/1997 | Dinh et al. |
| 5,605,696 A | 2/1997 | Eury et al. |
| 5,609,629 A | 3/1997 | Fearnot et al. |
| 5,616,608 A | 4/1997 | Kinsella et al. |
| 5,620,738 A | 4/1997 | Fan et al. |
| 5,624,411 A | 4/1997 | Tuch |
| 5,626,862 A | 5/1997 | Brem et al. |
| 5,637,113 A | 6/1997 | Tartaglia et al. |
| 5,651,986 A | 7/1997 | Brem et al. |
| 5,652,347 A | 7/1997 | Pouyani et al. |
| 5,670,507 A | 9/1997 | Rice et al. |
| 5,674,192 A | 10/1997 | Sahatjian et al. |
| 5,674,241 A | 10/1997 | Bley et al. |
| 5,674,242 A | 10/1997 | Phan et al. |
| 5,679,400 A | 10/1997 | Tuch |
| 5,697,967 A | 12/1997 | Dinh et al. |
| 5,700,286 A | 12/1997 | Tartaglia et al. |
| 5,702,754 A * | 12/1997 | Zhong ........................ 427/2.12 |
| 5,709,874 A | 1/1998 | Hanson et al. |
| 5,712,326 A | 1/1998 | Jones et al. |
| 5,716,406 A | 2/1998 | Farber |
| 5,716,981 A | 2/1998 | Hunter et al. |
| 5,733,925 A | 3/1998 | Kunz et al. |
| 5,739,237 A | 4/1998 | Russell et al. |
| 5,755,769 A | 5/1998 | Richard et al. |
| 5,776,184 A | 7/1998 | Tuch |
| 5,776,611 A | 7/1998 | Elton et al. |
| 5,779,732 A | 7/1998 | Amundson |
| 5,800,541 A | 9/1998 | Rhee et al. |
| 5,837,008 A | 11/1998 | Berg et al. |
| 5,874,417 A | 2/1999 | Prestwich et al. |
| 5,897,955 A | 4/1999 | Drumheller |
| 5,902,283 A | 5/1999 | Darouiche et al. |
| 5,955,588 A | 9/1999 | Tsang et al. |
| 5,972,199 A | 10/1999 | Heller et al. |

FOREIGN PATENT DOCUMENTS

| | | |
|---|---|---|
| EP | 0 106 004 | 4/1984 |
| EP | 0 166 998 | 1/1986 |
| EP | 0 274 846 | 7/1988 |
| EP | 0 294 905 | 12/1988 |
| EP | 0 389 632 | 10/1990 |
| EP | 0 395 098 | 10/1990 |
| EP | 0 407 965 | 1/1991 |
| EP | 0 439 908 | 8/1991 |
| EP | 0 470 246 | 2/1992 |

| | | |
|---|---|---|
| EP | 0 470 569 | 2/1992 |
| EP | 0 480 809 A2 | 4/1992 |
| EP | 0 480 809 A3 | 4/1992 |
| EP | 0 496 305 | 7/1992 |
| EP | 0 543 653 | 5/1993 |
| EP | 0 551 182 | 7/1993 |
| EP | 0 567 816 | 11/1993 |
| EP | 0 568 310 | 11/1993 |
| EP | 0 592 870 | 4/1994 |
| EP | 0 604 022 | 6/1994 |
| EP | 0 611 576 | 8/1994 |
| EP | 0 623 354 | 11/1994 |
| EP | 0 627 226 | 12/1994 |
| EP | 0 706 376 | 4/1996 |
| EP | 0 832 618 | 1/1998 |
| GB | 1 435 797 | 10/1973 |
| GB | 2 128 500 | 5/1984 |
| WO | WO 92/19289 | 12/1989 |
| WO | WO 90/01969 | 3/1990 |
| WO | WO 90/05162 | 5/1990 |
| WO | WO 90/13332 | 11/1990 |
| WO | WO 91/00163 | 1/1991 |
| WO | WO 91/07154 | 5/1991 |
| WO | WO 91/10424 | 7/1991 |
| WO | WO 91/11193 | 8/1991 |
| WO | WO 91/12779 | 9/1991 |
| WO | WO 91/19756 | 12/1991 |
| WO | WO 92/00747 | 1/1992 |
| WO | WO 92/09073 | 5/1992 |
| WO | WO 92/12717 | 8/1992 |
| WO | WO 92/15286 | 9/1992 |
| WO | WO 92/19290 | 11/1992 |
| WO | WO 93/06792 | 4/1993 |
| WO | WO 93/11120 | 6/1993 |
| WO | WO 94/21308 | 9/1994 |
| WO | WO 95/03795 | 2/1995 |
| WO | WO 96/03092 | 2/1996 |
| WO | WO 96/03984 | 2/1996 |
| WO | WO 96/25176 | 8/1996 |
| WO | WO 96/26689 | 9/1996 |
| WO | WO 97/33552 | 9/1997 |
| WO | WO 98/36784 | 8/1998 |
| WO | WO 99/40954 | 8/1999 |

OTHER PUBLICATIONS

Bruck, Stephen D., "Interactions of Synthetic and natural surfaces with blood in the Physiological Environment," J. Biomed. Mater. Res. Symposium, No. 8 (1997) pp. 1–21.

Cox, David A., M.D. et al., "Effect of Local Delivery of Heparin and Methotrexate on Neointimal Proliferation in Stented Porcine Coronary Arteries", Cornoray Artery Disease, vol. 3, No. 3, Mar. 1992, pp. 237–248.

Cox, D. A. et al., "Local Delivery of Heparin and Methotrexate Fails to Inhibit In Vivo Smooth Muscle Cell Proliferation", Supplement to Circulation Abstracts From the 64th Scientific Sessions, vol. 84, No. 4, Abstract No. 0284, 1991, p. II–71.

Dev, V. et al. "Kinetics of Drug Delivery to the Arterial Wall Via Polyurethane Coated Removable Nitinol Stent–Comparative Study of 2 Drugs", Circulation Abstracts From the 66th Scientific Sessions, vol. 88, No. 4, Part 2, Abstract No. 1657 (1993) p. I–3.

Esquivel, Carlos O., M.D. et al., "Reduced Thrombogenic Characteristics of Expanded Polytetrafluoroethylene and Polyurethane Arterial Grafts After Heparin Bonding," Surgery, Jan. 1984, pp. 102–107.

Guyton, John R. et al., "Inhibition of Rat arterial Smooth Muscle Cell Prolicferation by Heparin," Circulation Research, vol. 46, No. 5, May 1980, pp. 625–634.

Jampel, Henry D., M.D. et al., "In Vitro Release of Hydrophobic Drugs From Polyanhydride Disk", Ophthalmic Surgery, dated prior to Jan. 8, 1991.

Kawahito, Koji et al., "Heparin Coated Percutaneous Cardiopulmonary Support for the Treatment of Circulatory Collapse After Cardiac Surgery," ASAIO Journal, vol. 40, No. 4, Oct.–Dec. 1994, pp. 972–976.

Kishida, Akio et al., "Immobilization of Human Thrombomodulin onto Biomaterials," ASAIO Journal, Slide Forum—Materials 4 (1994) pp. M840–M845.

Lambert, T. et al., "A New Method For Arterial Drug Delivery Via Removable Stent", JACC, vol. 21, No. 2, Abstract No. 834–2 (1993) p. 483A.

Lambert, T. et al., "Localized Arterial Drug Delivery From a Polymer Coated Removable Metallic Stent: Kenetics and Bioactivity of Forskolin", Circulation Abstracts From the 66th Scientific Sessions, vol. 88, No. 4, Part 2, Abstract No. 1659 (1993) p. I–3.

Linhardt, Robert J. et al., "Differential Anticoagulant Activity of Heparin Fragments Prepared Using Microbial Heparinase," The Journal of Biological Chemistry, vol. 257, No. 13, Jul. 10, 19xx, pp. 7310–7313.

Miyama, Hajime et al., "A New Antithrombogenic Heparinized Polymer," J. Biomed Mater. Res., vol. 11 (1977) pp. 251–265.

Moses, Marsha A. et al., Inhibitors of Angiogenesis, Review, The Children's Hospital Medical Center, Boston, MA, dated prior to Jan. 8, 1999.

Nichols, Allen B. et al., "Effect of Heparin Bonding on Catheter–induced Fibrin Formation and Platelet Activation," Circulation, vol. 70, No. 5, Nov. 1984, pp. 843–850.

Pitt, C. G. et al., "The Design of Controlled Drug Delivery Systems Based on Biodegredable Polymers", Progress in Contraceptive Delivery Systems, M T P Press, Lancaster, vol. 1 (1980) pp. 17–18.

Sheppeck, Richard A. et al., "Examination of the Roles of Glycoprotein Ib and Glycoprotein IIb/IIIa in Platelet Deposition on an Artificial Surface Using Clinical Antiplatelet Agents and Monoclonal Antibody Blockade," Blood, vol. 78, No. 3, Aug. 1, 1991, pp. 673–680.

Tang, Chris et al., "Regression of Collagen–Induced Arthritis with Taxol, A Microtubule Stabilizer", Arthritis Rheum., vol. 36, No. 9 (Suppl.) (1993) p. 42.

*"A Powerful Case For LOPID", Parke–Davis, dated prior to Jan. 8, 1999.

*Whitborne, Richard, Ph.D., Presentation at the 2nd International Coronary Stenting Summit (Mar. 1–2, 1991).

*Wilson, Dr. Joseph, "Thromboresistant Plastic Coating Treatment," Research Partners, Inc., Internet Article dated Jan. 21, 1991, 2 pages.

PEBAX® 3533 SA00 Base Polymer for Structural Hot Melt Adhesives.

STS Biopolymers Literature, Medical Device Coating, pp 1–3, dated Sep. 15, 1999.

C.R. Bard Inc. Literature, Bard Medical Division, pp 1–2, dated Sep. 14, 1999.

Sur Modics Inc. Literature, Wt Lubriciy & Antimicrobial Properties, pp 1–2, dated Sep. 15, 1999.

Gabriel et al., Uncover Urinary Tract Infections, 1997.

* cited by examiner

HYDROPHILIC COATING AND SUBSTRATES COATED THEREWITH HAVING ENHANCED DURABLITY AND LUBRICITY

CROSS-REFERENCE TO RELATED APPLICATIONS

This application is a Divisional of U.S. Ser. No. 09/876,556 now U.S. Pat. No. 6,558,798, filed Jun. 7, 2001, which is a Continuation-in-part of U.S. Ser. No. 09/457,955, filed Dec. 9, 1999 now U.S. Pat. No. 6,468,649, which is a Continuation-in-part of U.S. Ser. No. 08/929,948, filed Sep. 15, 1997, now U.S. Pat. No. 6,048,620, which is a Divisional of U.S. Ser. No. 08/392,141, filed Feb. 22, 1995, now U.S. Pat. No. 5,702,754, all of which are incorporated by reference herein.

FIELD OF THE INVENTION

This invention relates to a method of providing a substrate, particularly a medical device or a part of such device intended for introduction in the human body, with a hydrophilic coating which becomes lubricous when contacted with an aqueous fluid. Substrates, particularly medical devices, with such hydrophilic coatings are also provided.

BACKGROUND OF THE RELATED TECHNOLOGY

It is generally known to provide substrates, for instance medical devices or parts of such devices, with a hydrophilic coating for the purpose of reducing the friction when the device is introduced in an aqueous environment, such as the human body. Such hydrophilic coatings have also been referred to as lubricous or "slippery" coatings.

Catheters and other medical devices used for introduction in blood vessels, urethra, body conduits and the like and guide wires used with such devices are examples of article which may be provided with hydrophilic coatings. Catheters for balloon angioplasty and biopsy are specific examples of such catheters.

Substrates and medical articles or devices having a hydrophilic coating and methods for providing such substrates and articles or devices with hydrophilic coatings have been described in an abundant number of references, examples of which are mentioned below.

U.S. Pat. No. 4,119,094 discloses a method of coating a substrate with a polyvinylpyrrolidone-polyurethane interpolymer. In the disclosed method, a polyisocyanate and a polyurethane in an organic solvent, such as methyl ethyl ketone, are applied to a substrate. The organic solvent is evaporated to yield a treated substrate. Polyvinylpyrrolidone in yet another organic solvent is then applied to the treated substrate. The solvent evaporated to provide the substrate with a hydrophilic coating.

U.S. Pat. No. 5,091,205 discloses a method of providing a substrate with a hydrophilic coating in which the substrate is first contacted with a polyisocyanate solution and then contacted with a poly(carboxylic acid) solution. Oven drying is described as being used to remove the organic solvents from these solutions. Methyl ethyl ketone is the preferred solvent for the polyisocyanates and dimethyl formamide is the preferred solvent for the poly(carboxylic acid). It is mentioned that the polyisocyanates can be dispersed in a solvent/non-solvent mixture to form an oil-in-water emulsion in which case, however, the reactive isocyanate groups need to be protected by suitable chemical groups.

EP Patent No. 0 106 004 B1 discloses a method of forming a hydrophilic coating on a substrate by applying a coating from an organic solvent solution of a polyisocyanate to form a coupling coating followed by application of an organic solvent solution of a hydrophilic copolymer made from monomers selected from vinyl pyrrolidone, vinyl methyl ether or vinyl pyridine and a monomer containing active hydrogen which will react with isocyanate to form a covalent bond between the coupling coating and the hydrophilic copolymer. Preferred organic solvents are described as being methyl ethyl ketone, chloroform and ethyl lactate.

EP Patent No. 0 166 998 B1 discloses a method for treating the surface of a medical instrument. The surface is treated with a solution of a polymer having a reactive functional group in an organic solvent followed by treatment with a water-soluble polymer selected from maleic anhydride polymers, cellulosic polymers, polyethylene oxide polymers, and water-soluble nylons or derivatives thereof to covalently bond the reactive functional group with the water-soluble polymer after which the treated substrate is optionally contacted with water. Certain ketones, aromatics, esters, ethers and halogenated hydrocarbons are described as being the organic solvent necessary for forming the solution.

U.S. Pat. No. 5,077,352 discloses a method in which a flexible, lubricous, organic polymeric coating is formed by applying a mixture of an isocyanate, a polyol and a poly (ethylene oxide) in a carrier liquid to a surface to be coated. The carrier liquid is removed and the mixture reacts to form a polyurethane coating with associated poly(ethylene oxide). Methylene chloride, chloroform, dichloroethane, acetonitrile, dichloroethylene, and methylene bromide are mentioned as suitable carrier liquids.

International Patent Applications Nos. PCT/EP92/00918, PCT/EP92/00919, and PCT/DK92/00132 disclose methods for providing different medical devices having a polyurethane surface with a coating of a hydrophilic poly(meth) acrylamide. Before application of the hydrophilic coating the substrate is treated with a compound having functional groups capable of reacting with the polyurethane and the poly(meth)acrylamide, respectively, typically a di or higher functionality isocyanate in an organic solvent.

A drawback of the methods according to the above-mentioned references is that the provision of the hydrophilic coating usually involves the use of organic solvents or toxic chemicals, for instance polyisocyanates, which can present environmental problems and/or health risks. In order to avoid the use of solvents some non-solvent methods have been developed.

EP Patent Application No. 92100787.8, Publication No. EP 0 496 305 A2, discloses a method for preparing a shaped medical article provided with a lubricous coating. A coating composition comprising a blend of polyurethane and polyvinylpyrrolidone is co-extruded with a substrate polymer to give a shaped article having thereon a layer of the coating composition which becomes lubricous when contacted with water.

U.S. Pat. No. 5,041,100 discloses a method for coating a substrate with a mixture of poly(ethylene oxide) and an aqueous dispersion of structural plastic material, e.g., polyurethane. As indicated in column 2, lines 15–21, the poly (ethylene oxide) is admixed without crosslinking in intimately dispersed relation with the structural plastic material to provide a hydrophilic component to the system, which may leach to the surface, or which may be entrapped adjacent the surface to provide a hydrophilic character thereto and reduce friction, particularly when hydrated.

The methods described in the above-mentioned references have the drawback that the interpolymer network physically attaching the hydrophilic polymer to the substrate often breaks down upon prolonged turbulent flow or soaking. Furthermore, the hydrophilic species can be washed away thereby rendering the article insufficiently lubricous.

Finally, International Patent Application No. PCT/DK91/00163 discloses a method of providing a medical instrument with a hydrophilic, low-friction coating, which method comprises the steps of forming an inner layer from an aqueous polymer emulsion and an outer layer from an aqueous solution of a water-soluble hydrophilic polymer and curing the two layers simultaneously following application of the outer layer by heating to a temperature of above 100° C.

The above method eliminates the use of organic solvents and results in a coating which is strongly attached to the substrate. However, the use of curing temperatures above 100° C. limits the use of the method, because many devices, for instance poly(ethylene terephthalate) (PET) balloon catheters cannot resist such temperatures.

SUMMARY OF THE INVENTION

The present invention is directed to a method of providing a substrate, particularly a medical device or a part of such device intended for introduction in the human body, with a hydrophilic coating becoming lubricous when contacted with an aqueous fluid, which method among others makes it possible to coat devices which are sensitive to high processing temperatures, such as (PET) balloon catheters. The hydrophilic polymer becomes covalently bonded to the polymers of an underlying coating to form a unitary hydrophilic coating.

In one aspect of the present invention a unitary hydrophilic coating is formed from multiple aqueous dispersions of emulsions of polymers. A first coating composition is formed from an aqueous dispersion or emulsion of a polymer having organic acid functional groups and a first polyfunctional crosslinking agent having functional groups being capable of reacting with organic acid groups. This composition is applied to a substrate or a portion of the substrate and dried to form a base coating. A second coating composition is formed from an aqueous solution or dispersion of a hydrophilic polymer having organic acid functional groups, a second polymer having organic acid functional groups, and a second polyfunctional crosslinking agent having functional groups being capable of reacting with organic acid groups. This composition is dried to effectuate covalent bonding of the hydrophilic polymer and the second polymer to the first polymer of the first coating composition through the first or the second crosslinking agents to form a unitary hydrophilic coating of the present invention.

In another aspect of the present invention, a third coating composition is applied to the above-described dried compositions to provide another embodiment of a unitary hydrophilic coating of the present invention. The coating formed from the above-described dried compositions is contacted with a third aqueous coating composition formed from an aqueous solution or dispersion of a second hydrophilic polymer having organic acid functional groups. This composition is dried to effectuate covalent bonding of the second hydrophilic polymer to the first hydrophilic polymer or the second polymer of the dried second coating composition through the second crosslinking agent.

The polymers, the hydrophilic polymers and the crosslinking agents of the different compositions may be the same or may be different.

The method according to the present invention includes coating a substrate or a portion of a substrate with a first aqueous coating composition having an aqueous dispersion or emulsion of a first polymer having organic acid functional groups and a first polyfunctional crosslinking agent having functional groups being capable of reacting with organic acid groups, and drying the first coating composition to obtain a substantially water-insoluble coating layer still including functional groups being reactive with organic acid groups. This is followed by contacting the dried coating layer with a second aqueous coating composition having an aqueous solution or dispersion of a hydrophilic polymer having organic acid functional groups, a second polymer having organic acid functional groups, and a second polyfunctional crosslinking agent having functional groups being capable of reacting with organic acid groups, and drying to effectuate covalent bonding of the hydrophilic polymer and the second polymer to the first polymer of the first coating composition through the first or second crosslinking agents to form a hydrophilic coating. In the method of the present invention the first polymer and second polymer may be the same or different. Furthermore, the first crosslinking agent and second crosslinking agent may be the same or different.

In another aspect of the present invention, the above-described method may further include the step of contacting the hydrophilic coating with a third aqueous coating composition having an aqueous solution or dispersion of a second hydrophilic polymer having organic acid functional groups, and drying the combined coatings to effectuate covalent bonding of the second hydrophilic polymer to the first hydrophilic polymer or the second polymer of the hydrophilic coating through the second crosslinking agent. In this method of the present invention the hydrophilic polymer in the second aqueous coating composition and second hydrophilic polymer in the third aqueous coating composition may be the same or different.

Included as an aspect of the present invention is an implantable medical device having a substrate or a portion of a substrate coated with a cured unitary hydrophilic polymeric composition.

DETAILED DESCRIPTION OF THE INVENTION

The present invention is a method for providing a unitary hydrophilic coating formed from multiple aqueous dispersions or emulsions of polymer compositions, coating compositions formed by the inventive method, and substrates or parts of substrates coated with the inventive compositions. The compositions include a polymer having reactive organic acid functional groups present. Polyfunctional crosslinking agents capable of reacting with the organic acid functional groups of the polymer are also included in some or all of the compositions. The polymer composition which forms the exterior surface of the unitary coating includes a hydrophilic polymer to provide lubricity upon contact with an aqueous medium. As compared to the prior art, the inventive compositions do not contain organic solvents which have to be removed prior to use within the human body.

As described further herein, one polymeric composition is substantially crosslinked prior to the application of another polymeric composition. Sufficient functional groups remain from the crosslinking agent to participate in covalent bonding of the polymers in the different compositions to form a unitary, covalently bonded coating. This covalent bonding allows for excellent adhesion of the lubricous, hydrophilic coating of the present invention. The coating has excellent wear resistance, lubricity and can be applied in extremely thin layers so as not to affect the mechanical properties of the substrate to which it is applied. This is particularly important when the coating is to be applied to a thin-walled inflatable balloon on a balloon catheter used for angioplasty. The crosslinking agent, however, need not be present in each coating composition, but a coating composition should either contain a cross-linking agent or be proximally placed to a composition that does contain a crosslinking agent. For instance, only one of adjacently positioned coating compositions need to contain a crosslinking agent to effectuate bonding to form a unitary coating.

The polymers contained in the different compositions may be selected from any number of polymers recited herein. Of particular preference to compositions forming interior portions of the coating, however, are the water-borne polyurethane polymers and polyacrylic acid polymers. When dried, these polymers are not water soluble and provide a dried composition having good film characteristics, such as mechanical strength.

Hydrophilic polymers may also be selected from a wide variety of polymers which can be covalently bonded to different coating compositions due to the presence of their organic acid functionality. Of particular preference are the polyacrylic acid polymers and the acrylamide-acrylic acid copolymers, and these hydrophilic polymers should be near or at the exterior surface of the coating to provide lubricity thereat. When dried these hydrophilic polymers become lubricious upon contact with an aqueous solution.

As previously mentioned, medical devices which are at least partially coated with the coatings of the present invention have particular advantages over the prior art in that they can easily be inserted into the body with less frictional resistance due to the lubricous characteristics of the outer coating. Additionally, the adherence of the hydrophilic coating or coatings is improved over the prior art due to the covalent bonding which occurs between the coating layers. As mentioned herein, the coating of angioplasty inflatable balloons, which are an integral part of angioplasty balloon catheters, is one specific application intended for the coatings of the present invention. Additionally, other medical devices such as guide wires and the like are contemplated. The devices need not necessarily be intended for use inside the body, and exterior uses are also contemplated.

In the present context the term "organic acid group" is meant to include any groupings which contain an organic acidic ionizable hydrogen. Examples of functional groupings which contain organic acidic ionizable hydrogen are the carboxylic and sulfonic acid groups. The expression "organic acid functional groups" is meant to include any groups which function in a similar manner to organic acid groups under the reaction conditions, for instance metal salts of such acid groups, particularly alkali metal salts like lithium, sodium and potassium salts, and alkaline earth metal salts like calcium or magnesium salts, and quaternary amine salts of such acid groups, particularly quaternary ammonium salts.

The polymer having organic acid functional groups, which is included in the first aqueous coating composition, will be selected duly paying regard to the nature of the substrate to be coated. Typically the polymer in the first coating composition will be selected from homo- and copolymers including vinylic monomer units, polyurethanes, epoxy resins and combinations thereof. The polymer in the first coating composition is preferably selected from polyurethanes, polyacrylates, polymethacrylates, polyisocrotonates, epoxy resins, acrylate-urethane copolymers and combinations thereof having organic acid functional groups. In a particularly preferred embodiment of the method according to the invention the polymer in the first coating composition is selected from homo- and copolymers having a substantial amount of organic acid functional groups in their structure, which may act as an internal emulsifier. A specific class of polyurethanes which may be used in the first coating composition are the so-called water-borne polyurethanes, among which are the so-called internally emulsified water-borne polyurethane containing carboxylic acid groups and/or sulfonic acid groups, optionally as salts of such groups, as internal emulsifiers are particularly preferred.

Examples of water-borne polyurethanes are those supplied under the tradename NeoRez by Zeneca Resins, for instance NeoRez-940, NeoRez-972, NeoRez-976 and NeoRez-981; under the tradename Sancure by Sanncor, for instance Sancure 2026, Sancure 2710, Sancure 1601 and Sancure 899; under the tradenames U21 and U21X by B.F. Goodrich; and under the tradenames Bayhydrol LS-2033, Bayhydrol LS-2100, Bayhydrol LS-2990 by Bayer AG.

Another specific class of polymers which have shown particularly useful in the first coating composition are acrylate-urethane copolymers, for instance the acrylic urethane copolymer dispersions supplied under the tradenames NeoPac E-106, NeoPac E-121, NeoPac E-130 and NeoRez R-973 by Zeneca Resins.

The concentration of the polymer in the first coating composition is usually from about 2 to about 60% by weight and preferably from about 5 to about 40% by weight calculated as solids of polymer compared to the total weight of the first coating composition.

In addition to one or more polymers having organic acid functional groups, the first aqueous coating composition may include one or more polyfunctional crosslinking agents having functional groups being capable of reacting with organic acid groups. Polyfunctional crosslinking agents having functional groups being capable of reacting with organic acid groups are known in the art. For instance such polyfunctional crosslinking agents have been used for external crosslinking of polyurethanes.

Particularly preferred polyfunctional crosslinking agents for use in the method according to the invention are polyfunctional aziridines and polyfunctional carboimides.

Polyfunctional aziridines and polyfunctional carboimides and their use as crosslinking agents are known in the art.

The crosslinking agent supplied by Zeneca Resins under the tradename NeoCryl CX 100 and the crosslinking agent supplied by EIT Industries under the tradename XAMA-7 are specific examples of polyfunctional aziridine crosslinking agents which may be used in the method according to the invention, and the crosslinking agent supplied by Union Carbide under the tradename Ucarlink XL-29SE is a specific example of a polyfunctional carboimide crosslinking agent which may be used in the method according to the invention.

Among the polyfunctional aziridines useful include the trifunctional aziridine of the following formula:

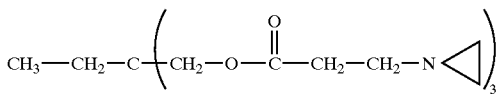

The polyfunctional crosslinking agent is preferably a crosslinking agent having more than two functional groups per molecule. Furthermore, it should be noted that a combination of polyfunctional crosslinking agents may be used in the method according to the invention.

The functional groups on the crosslinking agent serve at least two purposes. The first purpose is to crosslink the polymers in the first polymeric coating. The second purpose is to participate in covalent bonding with the organic acid groups present in a second or subsequent (hydrophilic) polymeric coating. As such, there must be sufficient functionality in the crosslinking agent to accomplish both purposes. That is, the amount of crosslinking agent used must be sufficient such that enough functional groups are present to substantially crosslink the first polymeric coating so that enough unreacted functional groups remain to covalently bond to the second (hydrophilic) polymeric layer.

One indication that insufficient functionals from the crosslinking agent are present is the inadequate bonding of the second layer. This is evidenced by the lack of wear resistance and such coatings can be easily wiped off the substrate to which they are applied.

The concentration of the crosslinking agent in the first coating composition is usually in the range from about 0.2 to about 30% by weight and preferably in the range from about 0.5 to about 20% by weight.

As is known in the art the first aqueous coating composition may include other conventional additives like leveling agents, various stabilizers, pH adjustment agents, defoaming agents, cosolvents, etc. if compatible with the intended use of the coated substrate.

The coating of the first aqueous coating composition is dried so as to obtain a substantially water-insoluble coating layer still including functional groups being reactive with organic acid groups. Hereafter, the obtained dried coating is contacted with a second aqueous coating composition comprising an aqueous solution or dispersion of components selected from the group consisting of a hydrophilic polymer having organic acid functional groups, a polymer having organic acid functional groups, a polyfunctional crosslinking agent having functional groups capable of reacting with organic acid groups, or combinations thereof. After applying this second coating, it is dried to form a hydrophilic coating. The polymers of this second composition become bonded to the polymer of the first coating composition through the crosslinking agents.

Hydrophilic polymers for use in hydrophilic lubricous coatings are known in the art. In the method according to the invention any hydrophilic polymer (homo- or copolymer or mixture of one or more of such polymers) may be used provided that it contains organic acid functional groups in its structure which can react with the polyfunctional crosslinking agent having functional groups being capable of reacting with organic acid groups to form a hydrophilic coating becoming lubricous when contacted with an aqueous fluid.

The hydrophilic polymer may comprise monomer units from one or more monomers having organic acid functional groups. Preferred examples of such monomers include acrylic acid, methacrylic acid and isocrotonic acid.

In addition to comprising monomer units from at least one monomer having organic acid functional groups, the hydrophilic polymer may contain monomer units from at least one hydrophilic monomer without any organic acid functional groups, such as vinylpyrrolidone and acrylamide. A preferred example of a copolymer for use in or as the hydrophilic polymer in the method according to the present invention is an acrylic acid-acrylamide copolymer. The acrylamide-acrylic acid copolymer supplied by Allied Colloids under the tradenames Versicol and Glascol. Versicol WN 23 and Glascol WN 33 are specific examples of such copolymers.

After the coating of the second aqueous coating composition is dried, it is contacted with a third aqueous coating composition comprising an aqueous solution or dispersion of a hydrophilic polymer having organic acid functional groups, after which the third coating is dried, the hydrophilic polymer of the third coating composition thereby becoming bonded to the polymers of the second coating composition through the crosslinking agent of the second coating composition.

The polymers, the hydrophilic polymers and the crosslinking agents of the different compositions may be the same or may be different. For example, the hydrophilic polymer, if any, in the second aqueous coating composition and hydrophilic polymer in the third aqueous coating composition may be the same or different. Similarly, the polymer in the first aqueous coating composition and the polymer, if any, in the second aqueous coating composition may be the same or different. Likewise, the crosslinking agent in the first aqueous coating composition and the crosslinking agent, if any, in the second aqueous coating composition may be the same or different.

The ability to become lubricous when hydrated is a critical aspect of the present invention. The degree of lubricity produced upon contact with aqueous medium will depend on a number of factors, including the type of hydrophilic polymer, its molecular weight, the exposure level to the aqueous medium, as well as the presence of agents which facilitate wetting. Among these, the molecular weight is the most important. The molecular weight range useful in the present invention will depend on the particular type of polymer chosen. The molecular weight of the hydrophilic polymer in the second coating composition will typically be in the range from about 100,000 to about 15 million, particularly from about 150,000 to about 10 million. Hydrophilic polymers having a molecular weight in the range from about 400,000 to about 10 million and particularly of approximately 7.5 million have been found particularly suitable for use in the method according to the invention. The aforementioned acrylamide-acrylic acid copolymer falls within this preferred molecular weight.

The concentration of the hydrophilic polymer in the second and third coating compositions will typically be from about 0.1 to 5% by weight, preferably from about 0.5 to about 3% by weight, calculated as solids of hydrophilic polymer compared to the total weight of the respective coating composition.

The second or intermediate coating composition may be formed from a combination of above two described first and third coating compositions. The ratio of these two compositions forming the intermediate coating composition may be varied. Desirably, a majority of the intermediate coating composition is formed from the third coating composition. Amounts from about 50 to about 99 percent of the third aqueous coating composition and from about 1 to about 50 percent of the first coating composition are useful as the intermediate coating composition. An intermediate coating composition having from about 80 to about 99 percent of the third composition and from about 1 to about 20 percent of the second composition is also useful. In one aspect of the present invention, the intermediate coating composition has about 96 percent of the third coating composition and about 4 percent of the first composition.

The intermediate composition does not necessarily have to be formed from a combination of the first and third coating compositions, but may be independently formed. The intermediate coating composition may include about 0.1 to about 5 weight percent polymer having organic acid functional groups, about 0.1 to about 5 weight percent hydrophilic polymer having organic acid functional groups, about 0.01 to about 10 weight percent crosslinking agent capable of reacting with the organic acid functional groups, or combinations thereof. For instance, as a non-limiting example, the intermediate coating composition may contain from about 0.1 to about 5 weight percent hydrophilic polymer having organic acid functional groups and about 0.01 to about 2 weight percent crosslinking agent capable of reacting with the organic acid functional groups. Moreover, the polymer, the hydrophilic polymer and the crosslinking agent of the intermediate coating composition may, individually or in combination, be the same or different from the constituents of the other coating compositions.

In one aspect of the present invention, a unitary hydrophilic coating may be formed from a first coating composition, such as described above, which does not contain a crosslinking agent. Such a first coating composition adheres to the surface of a substrate upon drying. Crosslinking agent contained in a subsequently applied coating composition will provide covalent bonding among the polymers contained in the two compositions. Thus, a hydrophilic coating composition may be formed from a base polymeric composition, an intermediate polymeric and/or hydrophilic composition and a terminal hydrophilic composition where only the intermediate composition contains a crosslinking agent. Moreover, the terminal or exterior dried composition may contain crosslinking agent or other polymers having organic acid functional groups in addition to having hydrophilic polymers having organic acid functional groups.

In a preferred embodiment of the method according to the invention the functional groups of the crosslinking agent are capable of reacting with the organic acid functional groups of the polymers and of the hydrophilic polymers at a temperature below 120° C. and preferably at a temperature below 100° C. The drying of the coating can be carried out at a temperature below 120° C. and preferably at a temperature below 100° C., although of course higher drying temperatures could be used if desired and compatible with the nature of the substrate to be coated. For instance a metal substrate could be dried at a higher temperature.

The present invention, however, is designed with the specific intent of being effective at relatively low temperatures and particularly at ambient or room temperature, to allow for use with heat sensitive substrates. In a further preferred embodiment of the method according to the invention the functional groups of the crosslinking agent are capable of reacting with the organic acid functional groups of the polymers and with the organic acid functional groups of the hydrophilic polymers at a temperature in the range of 10–70° C., preferably at a temperature in the range of 15–35° C. Such reactivity of the crosslinking agent makes it possible to coat the substrate at a temperature in the range of 10–70° C. and preferably at a temperature in the range of 15–35° C., such as at room temperature, although of course higher drying temperatures can be used, if desired.

The drying time will depend on the drying temperature, higher drying temperatures requiring shorter drying time and vice versa. It will be within the ordinary skill of a person skilled in the art to determine a suitable combination of drying temperatures and drying time for a specific coating.

In many cases drying at about room temperature for about 12 hours will be adequate.

Furthermore, it should be noticed that the functional groups of the crosslinking agent do not necessarily have to have the same reactivity towards the organic acid functional groups of the different polymers and hydrophilic polymers. Desirably, the drying conditions for the different coating compositions will be selected duly paying regard to the different reactivities.

The method according to the invention can be used for the coating of many different kinds of substrates. One field of use of particular interest is the coating of medical articles for use in or on the body, particularly catheters, guide wires or parts of such articles.

Balloon catheters, and particularly balloon catheters for percutaneous angioplasty are delicate articles which have proven difficult to coat by known methods. An important part of a balloon catheter is the inflatable balloon which in a balloon catheter for percutaneous angioplasty can have a very thin wall thickness, i.e., on the order of about 20 μm. In the condition in which the balloon catheter is introduced into a blood vessel the balloon is folded up into a multilayer construction. Therefore it is of great importance that a hydrophilic coating applied to the wall of such balloon minimize the increase in the wall thickness of the balloon. Furthermore, it is important that the balloon is made of a material which can be processed into a balloon of small wall thickness, still maintaining adequate strength and furthermore having the necessary biocompatibility. Polyethylene terephthalate (PET) possesses this combination of properties, but has been difficult to coat with a hydrophilic coating. Nevertheless, in accordance with the present invention it has been surprisingly discovered that a PET balloon having a wall thickness of as small as about 20 μm, can be effectively coated with a hydrophilic coating having a thickness of about 2–3 μm without damaging the balloon, and provides the required lubricity. The present invention advantageously accomplishes this because the process can be carried out using aqueous coating compositions, as opposed to organic solvent based systems, and drying takes place under mild conditions, e.g., simple air drying of the coatings at room temperature. For instance, as previously mentioned the drying of the combined coatings can be carried out at room temperature for about 12 to about 24 hours.

Moreover, as previously mentioned the method according to the invention can be used for the coating of many different substrates including substrates selected from polymeric substrates, non-polymeric substrates and combinations thereof. For example, among useful, but non-limiting, polymeric substrates include those selected from the group consisting of olefin polymers, particularly polyethylene, polypropylene, polyvinylchloride, polytetrafluoroethylene (PTFE), polyvinylacetate, and polystyrene; polyesters, particularly poly(ethylene terephthalate); polyurethanes; polyureas; silicone rubbers; polyamides, particularly nylons; polycarbonates; polyaldehydes; natural rubbers; polyether-ester copolymers; and styrene-butadiene copolymers.

In particular, the polymeric substrate can be selected from the group consisting of poly(ethylene terephthalate), polyurethanes, polyethylene, nylon 6, nylon 11 and polyether-ester copolymers.

Examples of useful non-polymeric substrate include those selected from the group consisting of ceramics, metals, glasses and the like.

Also, combinations of polymeric substrates and non-polymeric substrates as well as combinations of one or more polymeric substrates and/or one or more non-polymeric substrates can be coated by the method according to the invention.

The invention also relates to a coated substrate as obtainable by the method according to the invention and a medical device, particularly a catheter or a guide wire provided with a coating as obtainable by the method according to the invention.

A particularly preferred medical device according to the invention is a balloon catheter for percutaneous angioplasty having at least the balloon part provided with such coating.

The invention will be further illustrated in the following non-limiting examples representing presently preferred embodiments of the invention.

EXAMPLE 1

A first coating composition was prepared by adding the following ingredients successively to a glass beaker under proper agitation until thoroughly mixed.

| | |
|---|---|
| NeoRez R981: | 250 ml |
| Water: | 250 ml |
| 0.5% Fluorad FC-129 stock solution: | 10 ml |
| (prepared by diluting 1 ml Fluorad FC-129 in 100 ml of water) | |
| 34% NH$_4$OH: | 4 ml |
| NeoCryl CX 100: | 20 ml |

NeoRez R981 (from Zeneca Resins) is a polyester-based, aliphatic water-borne polyurethane containing carboxylic acid groups as internal emulsifier, which is stabilized by triethylamine (TEA) and has a solids content of 32% and a pH of 7.5–9.0 at 25° C. It contains a 5.3% N-methylpyrrolidone as cosolvent. NeoCryl CX 100 (from Zeneca Resins) is a polyfunctional aziridine crosslinking agent. Fluorad FC-129 (from 3M) is added as a leveling agent. Ammonium hydroxide is used to adjust the pH of the solution.

A second coating composition, as follows, was prepared:
1.2% aqueous solution of Versicol WN23: 400 ml The above solution was prepared by adding an appropriate amount of Versicol WN powder to water under agitation for several hours to obtain a clear homogeneous solution. Versicol WN23 (from Allied Colloids) is an acrylic acid-acrylamide copolymer having a molecular weight of 7.5×10$^6$.

A substrate was prepared by extruding a blend of two grades of polyether-ester block copolymer ARNITEL EM 740 and EM630 (from Akzo) with BaSO$_4$, into a tube. The tube was dipped into the first coating composition prepared above and dried at ambient temperature (room temperature) for 40 minutes. Then the tube was dipped in the second coating composition and dried at ambient temperature over night. The coated surface showed very good lubricous effect when contacted with water. Furthermore, the coating had very good wear resistance and abrasion resistance, the coating being strongly retained on the surface even under tough force.

EXAMPLE 2

In the same manner as in Example 1, a first coating composition was prepared using the following ingredients:

| | |
|---|---|
| U21X: | 250 ml |
| Water: | 100 ml |
| NeoCryl CX 100: | 10 ml |

U21X (from B.F. Goodrich) is a polyester-based, aliphatic polyurethane dispersion containing carboxylic acid groups as internal emulsifier and being stabilized by TEA. The dispersion has a solids content of about 30%, a pH of 8.5 and a viscosity of 75 cps. The dispersion includes 8.3% N-methylpyrrolidone as cosolvent.

A second coating composition as follows was prepared in the same manner as in Example 1:
1.2% Versicol WN23 aqueous solution A balloon catheter having a poly(ethylene terephthalate) (PET) balloon was coated with the above coating compositions in the following manner. The PET balloon was inflated and coated with the first coating composition by dipping and dried at ambient temperature for 30 minutes. Then the balloon was dipped in the second coating composition and dried at ambient temperature over night. The resultant dried coating was sterilized by electron beams at a dose of 2×25 KGray.

The obtained coating showed excellent slipperiness and lubricity when contacted with saline. The wear resistance and the abrasion resistance of the coating were also excellent.

EXAMPLE 3

A first coating composition was prepared by adding the following ingredients successively to a glass beaker under proper agitation until thoroughly mixed.

| | |
|---|---|
| Bayhydrol LS-2033 | 460 g |
| Neocryl CX-100 | 40 g |

A second coating composition was prepared as follow:

| | |
|---|---|
| 1% Glascol WN33 aqueous solution | 382.5 g |
| 30% sodium chloride aqueous solution | 1.5 g |
| Bayhydrol LS-2033 | 15.5 g |
| Neocryl CX-100 | 0.5 g |

Proper amount of ammonium hydroxide was added to the above thoroughly mixed fluid to adjust the pH of the fluid to 8.5.

A third coating composition was prepared as follow:

| | |
|---|---|
| 1% Glascol WN33 aqueous solution | 398 g |
| 30% sodium chloride aqueous solution | 2 g |

Proper amount of ammonium hydroxide was added to the above mixed fluid to adjust the pH of the fluid to 9.5.

A polyurethane catheter tubing made of Tecothane was dipped into the first coating fluid air dried for 15 minutes. The tubing was then dipped into the second coating fluid and air dried for 20 minutes. Finally the tubing was dipped into the third coating fluid and air dried for 30 minutes. The finished part was further dried at ambient temperature for 24 hours. The coating was very slippery when hydrated.

EXAMPLE 4

A glass slide was coated using the following coating compositions and the same coating procedures and drying conditions as in Example 1.

First coating composition:

| | |
|---|---|
| NeoRez R-940: | 100 ml |
| NeoCryl CX 100: | 4 ml |

NeoRez R-940 (from Zeneca Resins) is a polyether-based, aromatic water-borne polyurethane.

Second coating composition:

| | |
|---|---|
| 1.2% Versicol WN23 Aqueous solution: | 400 ml |

The coating showed excellent slipperiness and lubricity when contacted with water.

EXAMPLE 5

A first coating composition was prepared by adding the following ingredients successively to a glass beaker under proper agitation until thoroughly mixed.

| | |
|---|---|
| Bayhydrol LS-2033 | 100 g |
| Water | 400 g |
| Neocryl CX-100 | 20 g |

Ammonium hydroxide was used to adjust the pH of the mixed fluid to 8.5.

A second coating composition was prepared as follow:

| | |
|---|---|
| 1% Glascol WN33 aqueous solution | 160 g |
| 30% sodium chloride aqueous solution | 0.5 g |
| Sancure 899 | 10 g |
| Neocryl CX-100 | 2 g |
| Water | 50 g |

Proper amount of ammonium hydroxide was added to the above thoroughly mixed fluid to adjust the pH of the fluid to 8.5.

A third coating composition was prepared as follow:

| | |
|---|---|
| 1% Glascol WN33 aqueous solution | 255 g |
| 30% sodium chloride aqueous solution | 1 g |
| Water | 45 g |

Proper amount of ammonium hydroxide was added to the above mixed fluid to adjust the pH of the fluid to 9.5.

A Nylon shaft was dipped into the first coating fluid air dried for 5 minutes. The tubing was then dipped into the second coating fluid and air dried for 15 minutes. Finally the tubing was dipped into the third coating fluid and air dried for 15 minutes. The finished part was further dried at ambient temperature for 24 hours. The coating was very slippery when hydrated.

Glascol is an acrylic acid/acrylamide copolymer supplied by Allied Colloids of Ciba Specialty Chemical Holdings Inc.

EXAMPLE 6

Using the same coating procedures as described in Example 1, a PET substrate was coated with the following coating compositions:

First coating composition:

| | |
|---|---|
| Bayhydrol LS 2033: | 200 ml |
| NeoRez R-940: | 100 ml |
| Triethylamine: | 2 ml |
| Water: | 200 ml |
| NeoCryl CX 100: | 10 ml |

Second coating composition:

| | |
|---|---|
| 0.8% Versicol WN23 aqueous solution: | 400 ml |

The resulting coating showed excellent slipperiness and lubricity when contacted with water.

EXAMPLE 7

A glass plate was coated with the following coating compositions as described in the following.

First coating composition:

| | |
|---|---|
| Sancure 899: | 200 ml |
| NeoPac E121: | 100 ml |
| Acrysol TT-615: | 1 ml |
| (prediluted with equal weight of water) | |
| SAG 710: | 1 ml |
| 34% NH$_4$OH: | 4 ml |

Second coating composition:

| | |
|---|---|
| 1% Versicol WN23 aqueous solution: | 400 ml |

The first coating composition was brushed onto the glass plate and dried at ambient temperature for 1 hour. Then the second coating composition was sprayed onto the precoated glass surface and dried at ambient temperature over night. The obtained coating showed excellent slipperiness and lubricity when contacted with water.

Acrysol TT-615 is a thickener available from Rohm and Haas Company, and SAG 710 is a defoaming agent available from OSI Specialties, Inc.

EXAMPLE 8

First coating composition:

| | |
|---|---|
| Sancure 899: | 250 ml |
| 0.5% Fluorad FC-129 stock solution: | 10 ml |
| 34% NH$_4$OH: | 4 ml |
| Water: | 200 ml |
| Ucarlink XL-29SE: | 40 ml |

Second coating composition:

| | |
|---|---|
| 1% Versicol WN23 Aqueous solution: | 400 ml |

A balloon made from polyurethane (Impranil ELN, from Bayer A.G.) was dipped in the first coating composition and dried at ambient temperature for 40 minutes. Then the balloon was dipped in the second coating composition, dried at ambient temperature for 30 minutes and then dipped in the second coating composition once more. The coating was sterilized by EtO (ethylene oxide) sterilization. The coating showed excellent slipperiness and lubricity when contacted with water.

Ucarlink XL-29SE is a polyfunctional carboimide, available from Union Carbide.

EXAMPLE 9

A PET tube was coated with the following coating compositions as described in the following.

First coating composition:

| | |
|---|---|
| NeoPac E121: | 250 ml |
| Water: | 250 ml |
| Ucarlink XL-29SE | 40 ml |

Second coating composition:

| | |
|---|---|
| 1% Versicol WN 23 aqueous solution: | 400 ml |
| First coating composition: | 1 ml |

The PET tube was dipped in the first coating composition and air dried for 30 minutes. Then the precoated tube was dipped in the second coating composition and air dried for 30 minutes followed by drying at 60° C. for 24 hours. The coating showed excellent slipperiness and abrasion resistance when contacted with water.

In the foregoing the invention has been described by means of specific embodiments, but it will be understood that various changes and modifications may be performed without deviating from the scope and spirit of the invention.

NeoRez R-981; NeoRez R-940; NeoRez R-961; NeoRez R-972; NeoRez R-976; NeoRez R-973; NeoPac E-106; NeoPac E-130; NeoPac E-121; NeoCryl CX-100; Fluorad FC-129; U21; U21X; Glascol WN33; Versicol WN23; Bayhydrol LS-2033; Bayhydrol LS-2100; Bayhydrol LS-2952; Bayhydrol LS-2990; Sancure 899; Sancure 2710; Sancure 1601; Sancure 2026; Ucarlink XL-29SE; Acrysol TT-615 and SAG 710 are trademarks which may be registered in one or more of the designated countries.

What is claimed is:

1. A method of providing a substrate with a hydrophilic coating which becomes lubricous when contacted with an aqueous fluid, comprising:
   a) coating said substrate with a first aqueous coating composition comprising an aqueous dispersion or emulsion of a first polymer having organic acid functional groups and a first polyfunctional crosslinking agent having functional groups being capable of reacting with organic acid groups, and drying said first coating composition to obtain a substantially water-insoluble coating layer still including functional groups being reactive with organic acid groups; and
   b) contacting said dried coating layer with a second aqueous coating composition comprising an aqueous solution or dispersion of a hydrophilic polymer having organic acid functional groups, a second polymer having organic acid functional groups, and a second polyfunctional crosslinking agent having functional groups being capable of reacting with organic acid groups, and drying to effectuate covalent bonding of said hydrophilic polymer and said second polymer to said first polymer of the first coating composition through said first or said second crosslinking agents to form a hydrophilic coating;
   wherein said first polymer and said second polymer may be the same or different, and further wherein said first crosslinking agent and said second crosslinking agent may be the same or different.

2. A method of claim 1, wherein said second polymer is present in said second coating composition in an amount of up to 10 weight percent of said second coating composition.

3. A method of claim 1 wherein said second polymer in the second aqueous coating composition is the same as said first polymer in the first aqueous coating composition.

4. A method of claim 1 wherein said second crosslinking agent in the second aqueous coating composition is the same as said first crosslinking agent in the first aqueous coating composition.

5. A method of claim 1 further comprising:
   providing a quantity of said second polyfunctional crosslinking agent in said second aqueous coating composition so that said hydrophilic coating still includes functional groups being reactive with organic acid groups.

6. A method of claim 5 further comprising:
   contacting said hydrophilic coating with a third aqueous coating composition comprising an aqueous solution or dispersion of a second hydrophilic polymer having organic acid functional groups, and drying the combined coatings to effectuate covalent bonding of the second hydrophilic polymer to said first hydrophilic polymer or said second polymer of said hydrophilic coating through said second crosslinking agent;
   wherein said second hydrophilic polymer in the third aqueous coating composition and said hydrophilic polymer in the second aqueous coating composition may be the same or different.

7. A method of claim 6, wherein said second hydrophilic polymer in the third aqueous coating composition is the same as said hydrophilic polymer in the second aqueous coating composition.

8. A method of claim 1, wherein the organic acid functional groups are selected from free carboxylic or sulfonic acid groups, metal salts of such acid groups, particularly alkali metal salts, and quaternary amine salts of such acid groups.

9. A method of claim 1, wherein said first or said second polyfunctional crosslinking agent is selected from polyfunctional aziridines, polyfunctional carboimides and combinations thereof.

10. A method of claim 1, wherein said first or said second polyfunctional crosslinking agent is a crosslinking agent having more than two functional groups per molecule.

11. A method of claim 1, wherein said first or said second polymer is selected from homo- and copolymers having a substantial amount of organic acid functional groups in their structure.

12. A method of claim 1, wherein said first or said second polymer is selected from the group consisting of polyurethanes, polyacrylates, polymethacrylates, polyisocrotonates, epoxy resins, acrylate-urethane copolymers and combinations thereof.

13. A method according to claim 12, wherein said first or said second polymer comprises an acrylate-urethane copolymer and/or a polyurethane.

14. A method of claim 6, wherein said hydrophilic polymer in said second coating composition or said second hydrophilic polymer in said third coating composition comprises monomer units from at least one monomer having organic acid functional groups.

15. A method according to claim 14, wherein said hydrophilic polymer in said second coating composition or said second hydrophilic polymer in said third coating composition is selected from the group consisting of acrylic acid, methacrylic acid, isocrotonic acid and combinations thereof.

16. A method according to claim 14, wherein said hydrophilic polymer in said second coating composition or said second hydrophilic polymer in said third coating composition further comprises monomer units without any organic acid functional groups.

17. A method according to claim 14, wherein said hydrophilic polymer in said second coating composition or said second hydrophilic polymer in said third coating composition comprises an acrylamide-acrylic acid copolymer.

18. A method of claim 6, wherein the hydrophilic polymer in said second coating composition or said second hydrophilic polymer in said third coating composition have a molecular weight in the range from about 100,000 to about 15 million.

19. A method of claim 6, wherein the concentration of said hydrophilic polymer in said second coating composition or the concentration of said second hydrophilic polymer in said third coating composition is from about 0.1 to about 5% by weight solids content.

20. A method of claim 1, wherein the concentration of said first polymer in said first coating composition is from about 2 to about 60% by weight solids content.

21. A method of claim 1, wherein the concentration of said first crosslinking agent in said first coating composition is in the range from about 0.2 to about 30% by weight of said first coating composition and the concentration of said second crosslinking agent in the second coating composition is in the range from about 0.01 to about 10% by weight of said second coating composition.

22. A method of claim 6, wherein the functional groups of said first crosslinking agent and of said second crosslinking agent are capable of reacting with the organic acid functional groups of said first polymer, said second polymer, said hydrophilic polymer and said second hydrophilic polymer at a temperature below 120° C.

* * * * *